United States Patent [19]

Sawayanagi et al.

[11] Patent Number: 5,296,235
[45] Date of Patent: Mar. 22, 1994

[54] PLASTER PREPARATION

[75] Inventors: Yoichi Sawayanagi, Tokyo; Yutaka Kawamura, Narita, both of Japan

[73] Assignee: Dojin Iyaku-Kako Co., Ltd., Tokyo, Japan

[21] Appl. No.: 885,195

[22] Filed: May 19, 1992

[30] Foreign Application Priority Data

May 24, 1991 [JP] Japan .................. 3-120018

[51] Int. Cl.$^5$ .................................. A61K 9/14
[52] U.S. Cl. ...................... 424/486; 424/445
[58] Field of Search .............. 424/486, 445, 59; 514/774

[56] References Cited

U.S. PATENT DOCUMENTS

| 4,254,102 | 3/1981 | Kaplan | 424/59 |
| 4,695,465 | 9/1987 | Kigasawa | 514/774 |
| 4,801,458 | 1/1989 | Hidaka | 424/445 |

FOREIGN PATENT DOCUMENTS 0072462 2/1983 European Pat. Off. .
0143109 6/1985 European Pat. Off. .

Primary Examiner—Thurman K. Page
Assistant Examiner—William E. Benston, Jr.
Attorney, Agent, or Firm—Oblon, Spivak, McClelland, Maier & Neustadt

[57] ABSTRACT

A plaster comprising pranoprofen, a hydrophilic or hydrophobic base component, and an absorbefacient is disclosed. The plaster is effective for curing arthritis deformans, muscle ache, distention after external injuries, and aches. Since pranoprofen is administered away from gastrointestinal tracts, application of the plaster is not accompanied by side effects such as peptic ulcer, bleeding in constipation, and diarrhea. It can release pranoprofen constantly over a extended period of time.

2 Claims, 1 Drawing Sheet

PLASTER PREPARATION

BACKGROUND OF THE INVENTION

1. Field of the Invention

The present invention relates to a plaster preparation, and, more particularly, to an analgesic, anti-inflammatory plaster preparation comprising pranoprofen.

2. Description of the Background

Pranoprofen is popularly used in clinics in forms such as tablets, capsules, and the like as a non-steroidal antiinflammatory and analgesic drug due to its excellent anti-inflammatory and analgesic activity.

Non-steroidal anti-inflammatory and analgesic drugs usually exhibit a strong action to digestive organs after oral administration and, if dosed in a large amount, may cause side effects such as peptic ulcer and the like. Since pranoprofen exhibits such side effects only in a very limited degree, it is frequently used in clinics. However, pranoprofen is not always without risks of side effects; it is sometimes accompanied by side effects in digestive organs, such as peptic ulcer, bleeding in gastrointestinal tracts, constipation, diarrhea, and the like.

A cutaneous application of pranoprofen can reduce the side effects in digestive organs, since pranoprofen is administered away from gastrointestinal tracts where major side effects take place. In particular, for diseases involving local pains, such as arthritis deformans, muscle ache, distention after external injuries, aches, and the like, local administrations such as the cutaneous application are more advantageous for avoiding side effects and for maintaining a higher pranoprofen concentration at injured areas than the case where pranoprofen is dosed via circulating blood. Because of this, an ointment composition comprising pranoprofen and an organic solvent such as alcohol has been proposed in Japanese Patent Publication (ko-kai) No. 7115/1984. Pranoprofen can be well absorbed by the application of an ointment. The ointment, however, requires frequent applications, e.g., several times a day, in order to maintain its effects for a long period of time. In addition, the use of organic solvent is undesirable from the aspect of safety to the skin.

SUMMARY OF THE INVENTION

The present inventors have undertaken extensive studies in order to overcome the above problems and to promote the clinical utility of pranoprofen even more, and found that a use of pranoprofen as a plaster, by which pranoprofen can be dosed away from digestive tracts and in which a large amount of pranoprofen is contained without organic solvents, gives no side effects to digestive organs, is safe to the skin, and releases pranoprofen over a long period of time at a constant rate.

Accordingly, an object of the present invention is to provide a plaster comprising pranoprofen.

Other objects, features and advantages of the invention will hereinafter become more readily apparent from the following description.

DETAILED DESCRIPTION OF THE INVENTION AND PREFERRED EMBODIMENTS

Figure 1:
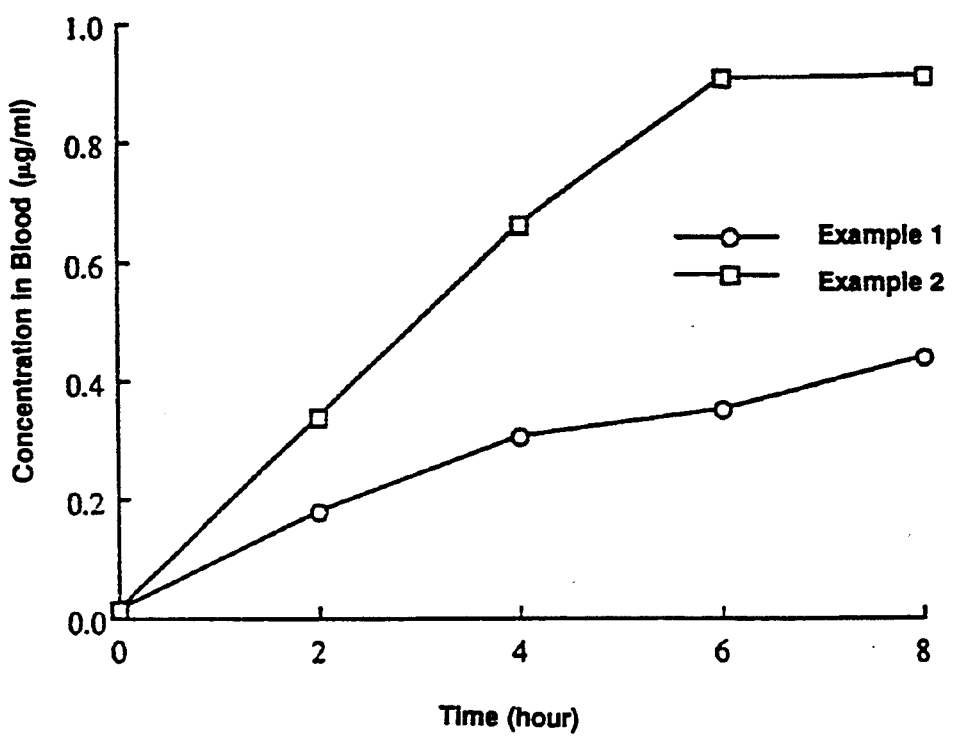
FIG. 1 is a drawing showing the relationship between the concentration of pranoprofen in blood and time in guinea pigs according to Test Example 1.

Bases used for the pranoprofen plaster of the present invention may be hydrophilic base components, typically water-soluble polymers, or hydrophobic base components, typically hydrophobic polymers Hydrophilic base components are more preferable for the cutaneous application of pranoprofen to arthritis deformans, muscle ache, and the like because of their capability of containing water with an effect of cooling injured areas.

There are no limitations to water-soluble polymers to be incorporated in the hydrophilic base; polyacrylic acid, sodium polyacrylate, carboxyvinyl polymer, sodium carboxymethyl cellulose, polyvinyl pyrrolidone, polyvinyl alcohol, hydroxypropyl cellulose, hydroxyethyl cellulose, ethyl cellulose, tragacanth gum, gum arabica, arginic acid, salts of arginic acid, xanthane gum, gelatin, and the like are preferably used. They may be used either individually or in combination, and may be incorporated in an amount of 0.2–20% by weight, and preferably 0.5–10% by weight, of the plaster composition.

The composition for the plaster may further contain an absorbefacient for promoting cutaneous absorption of pranoprofen. There are no specific limitations to absorbefacients used for this purpose; propylene glycol, diisopropyl adipate, 1-menthol, benzyl alcohol, and the like are preferably used. They are incorporated in an amount of 0.1–15% by weight, and preferably 0.5–10% by weight, of the plaster composition.

In addition to the above components, the composition for the plaster of the present invention may optionally contain such additives as commonly added to conventional hydrophilic base-type plaster preparations, such as polyhydric alcohols, e.g., glycerol, sorbitol; inorganic fillers, e.g., kaolin, titanium oxide; surfactants, e.g., polyoxyethylenesorbitan monooleate, sorbitan monooleate, polyethylene glycol monolaurate, polyoxyethylene hydrogenated castor oil; and the like. Furthermore, perfumes, stabilizers, pH modifiers, and the like may be added as required.

Any flexible woven or non-woven textiles, films, sheets and the like may be used as a backing material for the plaster composition comprising a hydrophilic base. Specific examples of such backing materials include woven polymer fibers, non-woven rayons, polyesters, polyolefins, polyurethanes, polymer films, foamed sheet materials, and the like. An anchor coat or the like may be provided if necessary.

Any films, including, for example, polyethylene films, polypropylene films, and polyester films, can be used for covering and protecting the composition applied to the backing sheets.

There are no specific limitations to hydrophobic polymers to be incorporated in the hydrophobic base composition; natural rubber, styrene-isoprene-styrene block copolymer (SIS), styrene-butadiene-styrene block copolymer (SBS), styrene-ethylene-butylene-styrene block copolymer (SEBS), ethylene-vinyl acetate copolymer, silicone, methylacrylate-2-ethylhexyl acrylate copolymer, and the like are preferably used. They may be incorporated in an amount of 30–99.5% by weight, and preferably 50–80% by weight, of the plaster composition.

The above-mentioned absorbefacients are used in the hydrophobic plaster compositions in the same manner as in the hydrophilic ones.

Any additives commonly added to conventional hydrophobic base-type plaster preparations may optionally be incorporated in the plaster composition of the present invention. Such additives include, for example, resins, e.g., chroman-indene resin, aromatic, or aliphatic hydrocarbon resins, modified rosin, polyterpen resin; waxes, e.g., solid paraffin, microcrystalline wax; esters, e.g., isopropyl myristate, glycerol esters of medium chain length fatty acid; plasticizers, e.g., liquid paraffin; and the like. Furthermore, perfumes, stabilizers, pH modifiers, and the like may be added as required.

Any flexible woven or non-woven textiles, films, sheets and the like may be used without limitation as a backing material for the plaster composition comprising a hydrophobic base. Specific examples of such backing materials include polymer films, e.g., polyvinyl chloride, polyurethane, polyethylene, ethylene-vinyl acetate copolymer, polystyrene; cotton textiles; non-woven fibers, e.g., non-woven cotton, non-woven polyester, non-woven polyolefin, non-woven polyurethane; foamed sheet materials; and the like. An anchor coat or the like may be provided if necessary.

Any films, including, for example, polyethylene films, polypropylene films, and polyester films, can be used for covering and protecting the composition applied to the backing sheets. If necessary, plaster films may be treated by releasing agents, by the corona discharge, or the like.

There are no specific limitations as to the method by which the plasters of the present invention are prepared. Usually, a pasty composition comprising 0.5–20% by weight of pranoprofen is first prepared, spread over a backing sheet, and covered by a protective film; or the pasty composition is spread over the protective film and the film is layered onto the backing sheet to transcript the paste onto the latter. If necessary, the plasters are stored in a tight container.

A safe, analgesic or anti-inflammatory plaster preparation exhibiting no side effects and releasing pranoprofen over a extended period can be provided according to the present invention.

Other features of the invention will become apparent in the course of the following description of the exemplary embodiments which are given for illustration of the invention and are not intended to be limiting thereof.

EXAMPLES

Example 1

One gram of polyoxyethylene (60) hydrogenated castor oil (HCO-60: trademark, manufactured by Nikko Chemicals. Co.), 2 g of benzyl alcohol, 2 g of diisopropyl adipate, and 5 g of propylene glycol were mixed with stirring under heating at 40° C., followed by the addition of 1 g of l-menthol to dissolve. 1 g of pranoprofen was added to the solution and the mixture was stirred to homogenize to obtain Mixture A. Mixture B was prepared by homogeneously dispersing 3 g of sodium carboxymethyl cellulose (CMC Daicel 1350: trademark, manufactured by Daicel Chemical Industries, Ltd.), 5 g of sodium polyacrylate (Aronvis SS: trademark, manufactured by Nihon Pure Chemical. Co.), and 0.1 g of ammonium alum in 15 g of concentrated glycerine (manufactured by Nippon Oil and Fats Co.). Mixture C was prepared by dispersing 4 g of kaolin (NN kaolin: trademark, manufactured by Tsuchiya Kaolin Co.) in 15 g of 70% aqueous solution of D-sorbitol. Mixtures A, B and C, and 40.9 g of purified water were mixed and kneaded to prepare a paste. The paste was spread over a sheet of non-woven textile (polyester-polyolefin, 100 g/cm$^2$; manufactured by Japan Vilene Co.) to produce a paste cover of 0.1 g/cm$^2$. The paste cover was covered with a polypropylene film to obtain a plaster preparation containing 1 mg/cm$^2$ of pranoprofen.

Example 2

9.9 g of polyvinyl alcohol (Kuraray Poval PVA120: trademark, manufactured by Kuraray Co.) was dissolved into 56.1 g of purified water heated to 90° C. and the solution was cooled to room temperature to obtain Mixture A. 5 g of benzyl alcohol, 2 g of diisopropyl adipate, and 5 g of propylene glycol were mixed with stirring under heating at 40° C., followed by the addition of 3 g of l-menthol to dissolve. 1 g of pranoprofen was added to the solution and the mixture was stirred to homogenize to obtain Mixture B. Mixtures A and B were mixed homogeneously and discharged into a mold to make a sheet of 0.1 g/cm$^2$. The sheet was sealed in a container and stored in a refrigerator at −20° C. for 24 hours, followed by thawing at 10° C. to obtain a plaster preparation containing 1 mg/cm$^2$ of pranoprofen.

Example 3

A dispersion of 5 g of pranoprofen in 5 g of propylene glycol was charged into 257 g of a silicone pressure-sensitive adhesive (a 35% solution, BIO-PSA Q7-2920: trademark, a product of Dow Corning Co.). The mixture was stirred to homogenize and coated over a releasable paper to obtain a sheet of paste of 2 mg/cm$^2$ on a dry basis. After drying, the paste was transcripted onto a surface of a polyvinyl chloride film to obtain a plaster preparation containing 0.1 mg/cm$^2$ of pranoprofen.

Example 4

5 g of benzyl alcohol and 2 g of diisopropyl adipate were mixed with stirring at 30° C., followed by the addition of 0.5 g of l-menthol to dissolve. 5 g of pranoprofen was added to the solution and the mixture was stirred to homogenize to obtain Mixture A. Mixture B was prepared by homogeneously dispersing 5 g of sodium carboxymethyl cellulose (CMC Daicel 1570: trademark, manufactured by Daicel Chemical Industries, Ltd.), 2 g of sodium polyacrylate (Aronvis SS: trademark, manufactured by Nihon Pure Chemical. Co.), and 0.2 g of dried aluminum hydroxide in 20 g of concentrated glycerin (manufactured by Nippon Oil and Fats Co.). Mixture C was prepared by dispersing 1 g of titanium oxide (TIPAQUE CR-50: trademark, manufactured by Ishihara Industries Co.) in 15 g of 70% aqueous solution of D-sorbitol. Mixtures A, B and C, and 44.3 g of purified water were mixed and kneaded to prepare a paste. The paste was spread over a polypropylene film to make a sheet of paste of 10 mg/cm$^2$, followed by transcription onto no-woven textile (rayon, 20 g/cm$^2$ laminated with a polypropylene film) to obtain a plaster preparation containing 0.5 mg/cm$^2$ of pranoprofen.

Example 5

A dispersion of 1 g of pranoprofen in 5 g of propylene glycol and 5 g of diisopropyl adipate was charged into 150.8 g of an emulsion of methylacrylate-2-ethylhexyl acrylate copolymer resin (Nicazole TS-620: trademark, a product of Nippon Carbide Industries, Ltd.) The mixture was stirred to homogenize and spread over a releasable paper to obtain a sheet of paste of 20 mg/cm$^2$ on a dry basis. After drying, the paste was transcripted onto a surface of a polyvinyl chloride film to obtain a plaster preparation containing 1 mg/cm$^2$ of pranoprofen.

Test Example 1

Pranoprofen plasters prepared in Examples 1 and 2 were applied to hair-cut backs of 3 male guinea pigs (Hartley, age 4 weeks, weight: 250–300 g) over 30 cm$^2$ (5×6 cm) areas. Changes in pranoprofen concentrations in blood sampled from cervical vein by a cannula were measured before the administration and at 2, 4, 6, and 8 hours after the administration. The results are shown in FIG. 1.

Obviously, numerous modifications and variations of the present invention are possible in light of the above teachings. It is therefore to be understood that within the scope of the appended claims, the invention may be practiced otherwise than as specifically described herein.

What is claimed is:

1. A plaster comprising pranoprofen, wherein the pranoprofen is not dissolved with an organic solvent, a hydrophilic base component and an absorbefacient comprising a mixture of propylene glycol, diisopropyladipate, and l-menthol, wherein each of the members of said mixture is present in an amount of from 0.1 to 15% by weight.

2. The plaster according to claim 1, further comprising benzyl alcohol.

* * * * *